United States Patent [19]

Omatsu et al.

[11] Patent Number: 5,684,167
[45] Date of Patent: Nov. 4, 1997

[54] PROCESS FOR PRODUCING 2-HYDROXY-4-METHYLTETRAHYDROFURAN

[75] Inventors: Toshihiro Omatsu, Kamisu-machi; Takashi Onishi, Hasaki-machi; Yasuo Tokitoh, Kawanishi, all of Japan

[73] Assignee: Kuraray Co., Ltd., Kurashiki, Japan

[21] Appl. No.: 659,833

[22] Filed: Jun. 7, 1996

[30] Foreign Application Priority Data

Sep. 6, 1995 [JP] Japan .................... 7-168165

[51] Int. Cl.$^6$ .................... C07D 307/20; C07C 29/132
[52] U.S. Cl. .................... 549/475; 568/454; 568/455; 568/861; 568/862
[58] Field of Search .................... 549/475; 568/861, 568/862, 454, 455

[56] References Cited

FOREIGN PATENT DOCUMENTS

| | | |
|---|---|---|
| 0 150 943 | 8/1985 | European Pat. Off. . |
| 0 155 002 | 9/1985 | European Pat. Off. . |
| 0 223 103 | 5/1987 | European Pat. Off. . |
| 0 303 060 | 2/1989 | European Pat. Off. . |
| 0 621 075 | 10/1994 | European Pat. Off. . |
| 0 627 399 | 12/1994 | European Pat. Off. . |
| 1565719 | 4/1980 | United Kingdom . |

OTHER PUBLICATIONS

Chemical Abstracts, vol. 116, No. 15, Apr. 13, 1992, AN 151552w, M. Matsumoto, et al., "Preparation of Dihydrofurans" & JP-A-03 261 776, Nov. 21, 1991.

Chemical Abstracts, vol. 103, No. 3, Jul. 22, 1985, AN 22459d, "2-Hydroxy-4-Methyl-Tetrahydropyran" & JP-A-60 019 781, Jan. 31, 1985.

Chemical Abstracts, vol. 116, No. 12, Mar. 30, 1992, AN 128646w, M. Matsumoto, "Preparation of 2-Hydroxytetrahydrofuran" & JP-A-03 261 775, Nov. 21, 1991.

Organometallics, vol. 11, pp. 3525–3533, 1992, A. Polo, et al., "Regioselective Hydroformylation of Cyclic Vinyl and Allyl Ethers with Rhodium Catalysts. Crucial Influence of the Size of the Phosphorous Cocatalyst".

Advances In Chemistry Series, vol. 230, pp. 395–418, 1992, A.A. Oswald, et al., "Electronic Effects on the Synthesis, Structure, Reactivity and Selectivity of Rhodium Hydroformylation Catalysts".

J. Prakt. Chem, vol. 314, pp. 840–850, 1972, C. Botteghi, et al., "Synthese von Optisch Aktiven und Racemischen 3–Alkyl-Tetrahydrofuranen".

Botteghi, Gazzetta Chimica Italiana, vol. 105, pp. 233–245 (1975).

Fell et al., Chemiker–Zeitung, vol. 101 (7/8), pp. 343–350 (1977).

*Primary Examiner*—Bernard Dentz
*Attorney, Agent, or Firm*—Oblon, Spivak, McClelland, Maier & Neustadt, P.C.

[57] ABSTRACT

2-Hydroxy-4-methyltetrahydrofuran is prepared by reacting 2-methyl-2-propen-1-ol with hydrogen and carbon monoxide in the presence of:

(a) a rhodium compound, and
(b) tris(substituted aryl)phosphite having an electronic parameter (v-value) of 2080 to 2090 cm$^{-1}$ and a steric parameter (θ-value) of 135° to 190° and having formula (1):

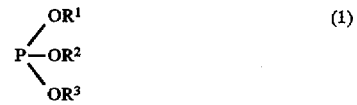

(1)

wherein R$^1$, R$^2$ and R$^3$ independently of each other represent a substituted aryl group having at least 7 carbon atoms, the ratio of said rhodium compound (a) to said tris(substituted aryl) phosphite (b) ranging from 110 to 1000 moles per 1 gram atom of rhodium in said rhodium compound (a).

7 Claims, No Drawings

PROCESS FOR PRODUCING 2-HYDROXY-4-METHYLTETRAHYDROFURAN

BACKGROUND OF THE INVENTION

1. Field of the Invention

The present invention relates to a process for producing 2-hydroxy-4-methyltetrahydrofuran by the reaction of 2-methyl-2-propen-1-ol (methallyl alcohol) with hydrogen and carbon monoxide in the presence of a rhodium compound. The 2-hydroxy-4-methyltetrahydrofuran obtained by the process of the present invention is useful as a synthetic intermediate for various fine chemicals such as pharmaceutical agents and agricultural chemicals. For example, the 2-hydroxy-4-methyltetrahydrofuran can be reduced to give 2-methyl-1,4-butanediol useful as a starting material for the synthesis of polymers such as polyester and fine chemicals.

2. Related Art of the Invention

The reaction of olefinically unsaturated organic compounds with hydrogen and carbon monoxide to give aldehydes, called hydroformylation or oxo-reaction, is an industrially useful synthetic process. For hydroformylation, generally, a cobalt compound or a rhodium compound is used as a catalyst. Among them, a rhodium compound is superior to a cobalt compound in the catalytic activity for hydroformylation and the selectivity for the resulting aldehydes. As such rhodium compound, a rhodium-carbonyl compound, a complex of rhodium with carbon monoxide, is generally used. However, the rhodium-carbonyl compound is an unstable and reactive compound. So, the rhodium-carbonyl compound is generally used as a stabilized complex modified with a ligand containing phosphorous, arsenic, antimony, etc. Then, an organic phosphorous compound such as triphenylphosphine is preferably used as such ligand.

Many processes for producing various tetrahydrofuranes by hydroformylating allylic alcohols have been reported. For example, British Patent No. 1493154 discloses a process for producing 2-hydroxytetrahydrofuran by hydroformylating allyl alcohol. According to the process of the British Patent, the hydroformylation is carried out at a low pressure of 4 kg/cm$^2$ or less, using a rhodium compound modified with triphenylphosphine as a catalyst, to attain a good selectivity for hydroformylated products. Additionally, a reference (J. Prakt. Chem., 314, 840–850 (1972)) describes a process for producing 1,4-butanediols which comprises hydroformylating allylic alcohols with RhCl(CO)(PPh$_3$)$_2$, a rhodium compound modified with triphenylphosphine, as a catalyst and subsequently reducing the resulting hydroformylated products. The reference also discloses that 2-hydroxytetrahydrofurans are formed as the hydroformylated products.

The present inventors have made attempts to carry out the hydroformylation process described in the above British Patent and the reference using 2-methyl-2-propen-1-ol as the starting material in order to produce 2-hydroxy-4-methyltetrahydrofuran, useful as a synthetic intermediate for various fine chemicals, in an industrial scale. Consequently, the inventors have found the following problems. More specifically, if the hydroformylation of 2-methyl-2-propen-1-ol is carried out at a low pressure of 4 kg/cm$^2$ or less by using, as a catalyst, a rhodium compound modified with a ligand of triphenylphosphine which has been most preferably used industrially, the reaction rate is extremely low. So, the concentration of such rhodium compound should essentially be high in order to carry out the hydroformylation of 2-methyl-2-propen-1-ol industrially. Since rhodium compounds are quite expensive, their use in a high concentration would be uneconomical unless they are recycled and reused for a long period. On the other hand, when the hydroformylation of 2-methyl-2-propen-1-ol is carried out at a high pressure of, for example, 100 kg/cm$^2$, the reaction rate is increased, but it is impossible to reduce the amount of rhodium compounds to the economically acceptable level.

SUMMARY OF THE INVENTION

It is an objective of the present invention to provide an industrially useful process for producing 2-hydroxy-4-methyltetrahydrofuran by hydroformylating 2-methyl-2-propen-1-ol in a high yield and economically with a low amount of a rhodium compound, while achieving an industrially satisfactory reaction rate.

As a result of an intensive study to attain the above objective, the inventors have found that the presence of a specific phosphorous compound in the reaction system can increase the reaction rate of the hydroformylation of 2-methyl-2-propen-1-ol even if a rhodium compound is used at a low concentration.

The present invention has been made in accordance with above finding and provides a process for producing 2-hydroxy-4-methyltetrahydrofuran which comprises making 2-methyl-2-propen-1-ol react with hydrogen and carbon monoxide in the presence of: (a) a rhodium compound, and (b) tris(substituted aryl) phosphite having an electronic parameter (v-value) of 2080 to 2090 cm$^{-1}$ and a steric parameter (θ-value) of 135° to 190° and being represented by the following general formula (1):

(1)

(wherein $R^1$, $R^2$ and $R^3$ independently represent a substituted aryl group with 7 or more carbon atoms) at a ratio of 110 to 1000 moles per 1 gram atom of rhodium.

DETAILED DESCRIPTION OF THE INVENTION

The present invention is described in detail.

In the present invention, the above two parameters are those defined according to the teachings of a reference (C. A. Tolman, Chem. Rev., 177, 313(1977)); the electronic parameter is defined as the frequency of the A1 infra-red absorption spectrum of the CO in an Ni(CO)$_3$L (wherein "L" is a ligand containing phosphorous) measured in dichloromethane; and the steric parameter is defined as the apex angle of a cylindrical cone, centered at a position of 2.28 angstroms apart from the center of the phosphorous atom, which just touches the Van der Waals radii of the atoms most externally present in the groups bonded to the phosphorous atom.

The tris(substituted aryl) phosphite to be used in the present invention should have an electronic parameter of 2080 to 2090 cm$^{-1}$ and a steric parameter of 135° to 190°. When a tris(substituted aryl) phosphite with either an electronic parameter or a steric parameter outside from the above described ranges is used, a high reaction rate or a high selectivity to the 2-hydroxy-4-methyltetrahydrofuran cannot be achieved in the hydroformylation of 2-methyl-2-propen-1-ol.

The $R^1$, $R^2$ and $R^3$ in the general formula (1) represent independently substituted aryl groups with 7 or more carbon atoms. The number of the carbon atoms of the $R^1$, $R^2$ and $R^3$ has no specific upper limit. Also, the substituted aryl groups may have any substituent which does not inhibit the hydroformylation. Such substituted aryl groups include, for example, tolyl group, xylyl group, t-butylphenyl group and the like.

Specific examples of the tris(substituted aryl) phosphite used in the present invention include tris(2-methylphenyl) phosphite, tris(2,6-dimethylphenyl) phosphite, tris(2-isopropylphenyl) phosphite, tris(2-phenylphenyl) phosphite, tris(2-t-butylphenyl) phosphite, tris(2-t-butyl-5-methylphenyl) phosphite, tris(2,4-di-t-butylphenyl) phosphite, di(2-methylphenyl)(2-t-butylphenyl) phosphite, di(2-t-butylphenyl)(2-methylphenyl) phosphite and the like. Among them, tris(2-t-butylphenyl) phosphite, tris(2-t-butyl-5-methylphenyl) phosphite, and tris(2,4-di-t-butylphenyl) phosphite are preferred.

The tris(substituted aryl) phosphite can be used alone or in combination.

The rhodium compound to be used in the present invention includes any rhodium compound that has a catalytic activity for hydroformylation or that can be converted to a compound having a catalytic activity for hydroformylation under the reaction conditions. Specific examples of the rhodium compounds used in the present invention include, for example, $Rh_4(CO)_{12}$, $Rh_6(CO)_{16}$, $Rh(acac)(CO)_2$, rhodium oxide, rhodium chloride, rhodium acetylacetonate, rhodium acetate and the like.

In the present invention, these rhodium compounds have extremely high catalytic activity for hydroformylation, so it is desirable to use these rhodium compound at a low concentration of 0.005 to 0.03 milligram atom/liter as converted into rhodium atom.

In the present invention, tris(substituted aryl) phosphite should be used in an amount within a range of 110 to 1000 moles per 1 gram atom of rhodium. When the tris(substituted aryl) phosphite is used in an amount of less than 110 moles per 1 gram atom of rhodium, the selectivity to 2-hydroxy-4-methyltetrahydrofuran is decreased. Further, the catalytic activity of the rhodium compound tends to be decreased by its thermal degradation during the separation of the product from the reaction mixture by vaporization. On the other hand, if the tris(substituted aryl) phosphite is used in an amount of higher than 1000 moles per 1 gram atom of rhodium, the reaction rate of the hydroformylation is likely to slow down.

The hydroformylation of 2-methyl-2-propen-1-ol is carried out generally at a temperature generally within a range of 60° to 150° C., preferably within a range of 80° to 130° C. When the reaction temperature is less than 60° C., the reaction rate is likely to slow down. On the other hand, if the reaction temperature is higher than 150° C., the catalytic activity of the rhodium compounds is likely to be deactivated.

The molar ratio of hydrogen and carbon monoxide in a gaseous mixture of hydrogen and carbon monoxide to be used in the present invention is selected generally from a range of 1/5 to 5/1 as an inlet gaseous ratio. Furthermore, small amount of gases inactive to the hydroformylation such as methane, ethane, propane, nitrogen, helium, argon, etc., can be present in the reaction system.

The reaction pressure is, depending on the reaction temperature, generally selected from a range of 60 to 150 atmospheres. If the reaction pressure is less than 60 atmospheres, the selectivity to 2-hydroxy-4-methyltetrahydrofuran tends to decrease. In addition, it is industrially advantageous, in view of equipment and operation, to maintain the reaction pressure at not more than 150 atmospheres. The reaction can be carried out either continuously or in a batch-wise process, in an agitator type reactor or a reactor of a bubble tower type.

In the present invention, the hydroformylation of 2-methyl-2-propen-1-ol can be carried out either in the absence of any solvent or in the presence of a solvent inert in the reaction system. Such solvent includes, for example, alcohols such as ethanol, butanol and ethylene glycol; saturated aliphatic hydrocarbons such as hexane, heptane and octane; aromatic hydrocarbons such as benzene, toluene, xylene, cumene, pseudo-cumene and ethylbenzene; esters such as ethyl acetate and dioctyl phthalate; and ethers such as tetrahydrofuran. The solvent can be used alone or in combination.

In the present invention, the presence of tertiary amine in the reaction system can suppress the acetalization of the hydroformylated product to lead high yield of 2-hydroxy-4-methyltetrahydrofuran. The tertiary amine is used preferably at the concentration of 100 mmoles or less per one liter of the reaction solution, and more preferably at the concentration of 20 mmoles or less per one liter of the reaction solution. When the concentration of a tertiary amine is higher than 100 mmoles per one liter of the reaction solution, the reaction rate is likely to slow down.

Specific examples of such tertiary amine include, for example, aliphatic tertiary amines such as triethylamine, tributylamine and trioctylamine; alkyl-substituted tertiary diamines such as N,N,N',N'-tetramethyl-1,2-diaminoethane; tertiary alkanol amines such as N,N-dimethyl ethanolamine and triethanolamine; cycloaliphatic tertiary amines such as N-methylpiperidine, N-methylpyrrolidine and N-methylmorpholine; and cyclic unsaturated tertiary amines such as pyridine and lutidine.

The 2-hydroxy-4-methyltetrahydrofuran obtained by the hydroformylation of 2-methyl-2-propen-1-ol can be separated from the reaction mixture by, for example, the vaporization of the reaction mixture under reduced pressure at a temperature of about 130° C. or less. Successive purification of the fraction containing 2-hydroxy-4-methyltetrahydrofuran obtained by vaporization with a known means such as distillation can isolate 2-hydroxy-4-methyltetrahydrofuran.

The whole or a part of the rhodium compound in the residuals after the vaporization can be reused for the hydroformylation of 2-methyl-2-propen-1-ol. Because rhodium compounds are quite expensive, such reuse of rhodium compounds is industrially advantageous.

The obtained 2-hydroxy-4-methyltetrahydrofuran can be converted to 2-methyl-1,4-butanediol by hydrogenation in the presence of hydrogenation catalyst.

As the starting material for the hydrogenation, either the fraction containing 2-hydroxy-4-methyltetrahydrofuran obtained by the vaporization of the reaction mixture of hydroformylation or 2-hydroxy-4-methyltetrahydrofuran isolated from the fraction can be used.

As the hydrogenation catalyst, a known catalyst for hydrogenation of aldehydes, such as Raney-nickel, Raney-cobalt, palladium black and copper chromite, can be used. In addition, a carried-type catalyst, such as nickel diatomaceous earth, palladium alumina, ruthenium carbon and the like, can be used. These catalysts may be partially modified with molybdenum, tungsten, iron, rhenium, manganese, and the like.

The hydrogenation catalyst is used in an amount of preferably 0.01 to 10% by weight of the reaction mixture as converted into the metal when the hydrogenation is carried out with the catalyst suspended in the reaction mixture.

The hydrogenation of 2-hydroxy-4-methyltetrahydrofuran is carried out at a temperature within a range of preferably 20° to 150° C., more preferably 50° to 150° C. In addition, the pressure of hydrogen can be within a range of preferably 1 to 100 atmospheres, more preferably 5 to 100 atmospheres.

The hydrogenation of 2-hydroxy-4-methyltetrahydrofuran can be carried out either in the absence of any solvent or in the presence of a solvent inert in the reaction system. Such solvent includes, for example, alcohols such as methanol, ethanol, propanol, butanol and octanol; saturated aliphatic hydrocarbons such as hexane, heptane and octane; ethers such as dibutyl ether, tetrahydrofuran and dioxane.

The hydrogenation of 2-hydroxy-4-methyltetrahydrofuran can be carried out in an agitator type reactor or a reactor of a bubble tower type with the catalyst suspended in the reaction mixture, or in a fixed-bed type reactor filled with a carried-type catalyst. Also, the hydrogenation reaction can be carried out either continuously or in a batch-wise process.

2-Methyl-1,4-butanediol, a hydrogenation product of 2-hydroxy-4-methyltetrahydrofuran, can be isolated with a known process comprising separating the hydrogenation catalyst from the reaction mixture by filtration, centrifuging and the like and subsequently purifying the product by a known means such as distillation.

EXAMPLES

Other features of the present invention will become apparent in the course of the following descriptions of the exemplary embodiments which are given for illustration of the present invention but are not intended to be limiting thereof.

Example 1

A 300-ml autoclave equipped with a gas inlet, a sampling port and an electromagnetic stirrer was charged with rhodium dicarbonylacetylacetonate (0.31 mg; 0.0012 mmole), tris(2,4-di-t-butylphenyl) phosphite (646 mg; 1 mmole) with an electronic parameter (v-value) of 2085.6 $cm^{-1}$ and a steric parameter (θ-value) of 175°, 2-methyl-2-propen-1-ol (100 ml; 1.19 mole at 25° C.) and triethanol amine (149 mg; 1 mmole) while avoiding their contact with air. Then, the inside of the autoclave was kept at a pressure of 90 kg/cm² under the purge of a gaseous mixture of hydrogen and carbon monoxide at a ratio of 3/1. Charging the gaseous mixture of hydrogen and carbon monoxide at a ratio of 3/1 into the autoclave and discharging the off-gas at 30 liters/h from the autoclave, the reaction mixture was stirred at 1,000 rpm and the temperature inside the autoclave was raised to 90° C. over 30 minutes. The hydroformylation reaction was effected at that state for 2.5 hours. Analysis of the reaction mixture with gas chromatography showed that the conversion of the 2-methyl-2-propen-1-ol (starting material) was 90%, while the selectivity to 2-hydroxy-4-methyltetrahydrofuran (hydroformylated product) was 87%.

Vaporization of the reaction mixture at 125° C. under the reduced pressure of 2.0 mmHg gave a fraction of 110 g.

Further, purification of the obtained fraction of 110 g by distillation under reduced pressure gave 86 g (0.84 mole) of 2-hydroxy-4-methyltetrahydrofuran.

Comparative Example 1

The hydroformylation of 2-methyl-2-propen-1-ol was carried out by the same procedures as in Example 1, except that triphenylphosphine (262 mg; 1 mmole) with an electronic parameter (v-value) of 2068.9 $cm^{-1}$ and a steric parameter (θ-value) of 145° was used instead of tris(2,4-di-t-butylphenyl) phosphite (646 mg). The conversion of 2-methyl-2-propen-1-ol was as small as 29% and the selectivity to 2-hydroxy-4-methyltetrahydrofuran was 89%.

Example 2

A 300-ml autoclave equipped with a gas inlet, a sampling port and an electromagnetic stirrer was charged with rhodium dicarbonylacetylacetonate (0.181 mg; 0.0007 mmole), tris(2,4-di-t-butylphenyl) phosphite (226 mg; 0.35 mmole), 2-methyl-2-propen-1-ol (100 ml; 1.19 mole at 25° C.) and triethanolamine (75 mg; 0.5 mmole) while avoiding their contact with air. Then, the inside of the autoclave was kept at a pressure of 60 kg/cm² under the purge of a gaseous mixture of hydrogen and carbon monoxide at a ratio of 1/1. Charging the gaseous mixture of hydrogen and carbon monoxide at a ratio of 1/1 into the autoclave and discharging the off-gas at 10 liters/h from the autoclave, the reaction mixture was stirred at 1,000 rpm and the temperature inside the autoclave was raised to 90° C. over 30 minutes. The hydroformylation reaction was effected at that state for 6 hours. Analysis of the reaction mixture with gas chromatography showed that the conversion of 2-methyl-2-propen-1-ol was 84%, while the selectivity to 2-hydroxy-4-methyltetrahydrofuran was 85%.

Comparative Example 2

The hydroformylation of 2-methyl-2-propen-1-ol was carried out by the same procedures as in Example 2, except that 45.2 mg (0.07 mmole) of tris(2,4-di-t-butylphenyl) phosphite was charged into the autoclave. The conversion of 2-methyl-2-propen-1-ol was 89% and the selectivity to 2-hydroxy-4-methyltetrahydrofuran was 57%.

Example 3

A 300-ml autoclave equipped with a gas inlet, a sampling port and an electromagnetic stirrer was charged with rhodium dicarbonylacetylacetonate (0.516 mg; 0.002 mmole), tris(2-t-butyl-5-methylphenyl) phosphite (520 mg; 1 mmole) with an electronic parameter (v-value) of 2085.6 $cm^{-1}$ and a steric parameter (θ-value) of 175° and 2-methyl-2-propen-1-ol (100 ml; 1.19 mole at 25° C.) while avoiding their contact with air. Then, the inside of the autoclave was kept at a pressure of 120 kg/cm² under the purge of a gaseous mixture of hydrogen and carbon monoxide at a ratio of 1/1. Charging the gaseous mixture of hydrogen and carbon monoxide at a ratio of 1/1 into the autoclave and discharging the off-gas at 10 liters/h from the autoclave, the reaction mixture was stirred at 1,000 rpm and the temperature inside the autoclave was raised to 90° C. over 30 minutes. The hydroformylation reaction was effected at that state for 3 hours. Analysis of the reaction mixture with gas chromatography showed that the conversion of 2-methyl-2-propen-1-ol was 91%, while the selectivity to 2-hydroxy-4-methyltetrahydrofuran was 90%.

Reference Example

A 1-liter autoclave equipped with a gas inlet, a sampling port and an electromagnetic stirrer was charged with 100 g of the fraction obtained by the vaporization of the reaction mixture of hydroformylation in Example 1, methanol (250 g), and Raney-nickel (5 g). The gas present in the autoclave was replaced with hydrogen, and then, the inside of the autoclave was kept at a pressure of 50 kg/cm² with hydrogen. The reaction mixture was stirred at 1,000 rpm and the temperature inside the autoclave was raised to 80° C. The hydrogenation reaction was effected at 80° C. for 3 hours, while keeping the pressure inside the autoclave at 50 kg/cm². Then the temperature inside the autoclave was raised to 100° C., and the hydrogenation reaction was continued at 100° C. for 3 hours. Analysis of the reaction mixture with gas chromatography showed that the starting material (2-hydroxy-4-methyltetrahydrofuran) was completely hydrogenated. The obtained reaction mixture of 85 g was purified by distillation to give 2-methyl-1,4-butanediol (70 g; 0.67 mole).

Obviously, numerous modifications and variations are possible in light of the above teachings. It is therefore to be understood that within the scope of the appended claims the present invention can be practiced otherwise than as specifically described herein.

What is claimed is:

1. A process for producing 2-hydroxy-4-methyltetrahydrofuran, which comprises:

reacting 2-methyl-2-propen-1-ol with hydrogen and carbon monoxide in the presence of:
   (a) a rhodium compound, and
   (b) tris(substituted aryl)phosphite having an electronic parameter (ν-value) of 2080 to 2090 cm⁻¹ and a steric parameter (θ-value) of 135° to 190° and having formula (1):

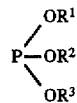

(1)

wherein $R^1$, $R^2$ and $R^3$ independently of each other represent a substituted aryl group having at least 7 carbon atoms, the amount of said tris(substituted aryl) phosphite (b) ranging from 110 to 1000 moles per 1 gram atom of rhodium in said rhodium compound (a).

2. The process of producing 2-hydroxy-4-methyltetrahydrofuran according to claim 1, wherein the concentration of said rhodium compound (a) in the reaction medium ranges from 0.005 to 0.03 milligram atom/liter, based on the rhodium atom content of said rhodium compound.

3. The process of claim 1, which comprises conducting said reaction under a pressure within the range of 60 to 150 atmospheres.

4. The process for producing 2-hydroxy-4-methyltetrahydrofuran according to claim 1, wherein the tris (substituted aryl) phosphite is at least one compound selected from the group consisting of tris(2-t-butylphenyl) phosphite, tris (2-t-butyl-5-methylphenyl) phosphite and tris (2,4-di-t-butylphenyl) phosphite.

5. The process for producing 2-hydroxy-4-methyltetrahydrofuran according to claim 2, wherein the tris (substituted aryl) phosphite is at least one compound selected from the group consisting of tris(2-t-butylphenyl) phosphite, tris(2-t-butyl-5-methylphenyl) phosphite and tris (2,4-di-t-butylphenyl) phosphite.

6. The process for producing 2-hydroxy-4-methyltetrahydrofuran according to any one of claims 4, 1, 2, 3 or 5, wherein a tertiary amine is present in the reaction system at a concentration of 100 mmoles or less per one liter of the reaction solution.

7. A process for producing 2-methyl-1,4-butanediol, which comprises hydrogenating the 2-hydroxy-4-methyltetrahydrofuran produced by the process according to claim 1.

* * * * *

UNITED STATES PATENT AND TRADEMARK OFFICE
CERTIFICATE OF CORRECTION

PATENT NO. : 5,684,167
DATED : November 4, 1997
INVENTOR(S) : Toshihiro OMATSU, et al.

It is certified that error appears in the above-identified patent and that said Letters Patent is hereby corrected as shown below:

On the title page, item [30], the Foreign Application Priority Data should be:

--Jun. 9, 1995  [JP]  Japan  ............  7-168195 --

Signed and Sealed this

Thirtieth Day of December, 1997

Attest:

BRUCE LEHMAN

Attesting Officer

Commissioner of Patents and Trademarks